United States Patent [19]

Magram

[11] Patent Number: 5,634,944

[45] Date of Patent: Jun. 3, 1997

[54] BODY MEMBRANE PROSTHESIS

[75] Inventor: Gary Magram, Greenville, Del.

[73] Assignee: The Nemours Foundation, Wilmington, Del.

[21] Appl. No.: 393,067

[22] Filed: Feb. 23, 1995

[51] Int. Cl.$^6$ .................................................. A61F 2/02
[52] U.S. Cl. ........................................ 623/11; 623/66
[58] Field of Search ................................ 623/8, 11, 16, 623/60; 600/37; 602/41, 42, 43, 45, 46, 58

[56] References Cited

U.S. PATENT DOCUMENTS

| | | | |
|---|---|---|---|
| 3,526,228 | 9/1970 | Lyng | 128/334 |
| 4,400,833 | 8/1983 | Kurland | 3/1 |
| 4,585,458 | 4/1986 | Kurland | 623/13 |
| 4,769,038 | 9/1988 | Bendavid et al. | 623/11 |
| 4,865,031 | 9/1989 | O'Keeffe | 128/334 R |
| 4,955,906 | 9/1990 | Coggins et al. | 623/8 |
| 4,994,084 | 2/1991 | Brennan | 623/11 |
| 5,053,046 | 10/1991 | Janese | 606/215 |
| 5,254,133 | 10/1993 | Seid | 606/215 |

OTHER PUBLICATIONS

Preclude Dura Substitute Advertisement, W.L. Gore & Associates, 1996.

Treatment and prevention of tethered and retethered spinal cord using a Gore–Tex surgical membrane, Inoue, H.K., et al., J. Neurosurg. 80:689–693, Apr., 1994.

*Primary Examiner*—Debra S. Brittingham
*Attorney, Agent, or Firm*—Jeffrey C. Lew

[57] ABSTRACT

A prosthesis and method are disclosed for patching openings in body membranes such as the dura mater. The novel prosthesis includes patch comprising a patch flange and a suture flange extending circumferentially around the patch. The patch is implanted inside the membrane such that the patch completely covers the opening to be closed. The lip of the opening laps the suture flange and is secured by sewing sutures through the suture flange and the lip, but not through the patch. Accordingly, the tissue underlying the patch is shielded from the suture threads and perforations by the patch flange. The patch is of lubricious and biologically inert materials that is effectively nonadhesive to scar growth which forms on healing wounds. Thus, the novel prosthesis reduces the potential for adhesion between the underlying tissues and the membrane due to scar formation following surgery, particularly surgery on the central nervous system.

17 Claims, 5 Drawing Sheets

5,634,944

BODY MEMBRANE PROSTHESIS

FIELD OF THE INVENTION

This invention relates generally to a surgically implantable prosthesis. More specifically, the invention pertains to a prosthetic device useful for repair of openings in body connective tissue membrane, such as the cranial or spinal dura mater.

BACKGROUND AND SUMMARY OF THE INVENTION

Surgery on the central nervous system requires entry through the dura mater, hereinafter "dura", a connective tissue membrane which surrounds the brain, spinal cord and nerve roots and which is filled with cerebrospinal fluid. To provide an opening, normally a section of dura is removed or the dura is cut to create a flap. Sometimes traumatic injury causes an opening in the dura. Quite often, the opening cannot be closed by sewing the dura to itself because the amount of remaining dura is insufficient or the quality of the dura near the opening is unsatisfactory. Closure may be achieved by covering the opening with a patch and attaching the patch to the dura with sutures.

Numerous perforations are made when the patch is sewn to the dura. This has the shortcoming that fibroblast growth in and around the perforations during normal healing leads to scar formation between the dura and underlying neural structures. The scar can cause underlying neural structures to adhere to the dura, preventing free movement of the structures within the cerebrospinal fluid. Such constraint may create tension involving a peripheral nerve or the spinal cord which produces pain. During normal body motion such constraint also is hypothesized to disturb the brain so as to increase frequency of seizures.

The need is not uncommon for the surgeon to reopen the dura in order to operate again. Reopening is occasionally required, for example, to remove a recurrent tumor or an epileptic portion of the brain. If substantial scar has connected the dura to the underlying neural structure, the surgeon may have to exercise extraordinarily great care to detach the dura without causing increased nerve damage during the later operation. Hence, conventional methods of patching a dural opening can increase the technical difficulty, and consequently, the morbidity of the procedure.

Attachment between dura and the underlying neural structure can be reduced by using patches of effectively nonadhesive materials. Still, some scar formation in the perforations and on suture threads which protrude through the patch and below the dura is expected to attach the dura to neural structure.

The primary object of the present invention is to provide a plentiful, tough, pliant and lubricious dural patch that generally minimizes scar tissue adhesion between body connective tissue membranes and adjacent organ tissue, and particularly, between dura and the underlying neural structures. More specifically, it is an objective to provide a dural patch which can be implanted in a manner that prevents scarring between the patch securement sutures and brain or spinal column.

Accordingly, there is provided an implantable prosthesis comprising
  a patch of lubricious, biologically benign material having a perimeter and having a patch flange extending inward from the perimeter by a lap distance; and
  a suture flange attached to one side of said patch, wherein said suture flange overlaps said patch flange.

There is further provided a process for closing an opening in a body membrane, said opening having a lip, including the steps of
  (i) placing within the opening and inside of the body membrane to completely close the opening, a prosthesis comprising:
    a patch of lubricious, biologically benign material having a perimeter and having a patch flange extending inward from the perimeter by a lap distance; and
    a suture flange attached to one side of said patch, wherein said suture flange overlaps said patch flange;
  (ii) lapping the lip and the suture flange; and
  (iii) attaching the suture flange to the lip.
Generally, the suture flange is attached to the lip by sewing sutures in a circuitous path along the lip of the opening at a location on the suture flange inboard of the patch perimeter and in a way that the sutures do not penetrate the patch.

DETAILED DESCRIPTION

Figure 1:
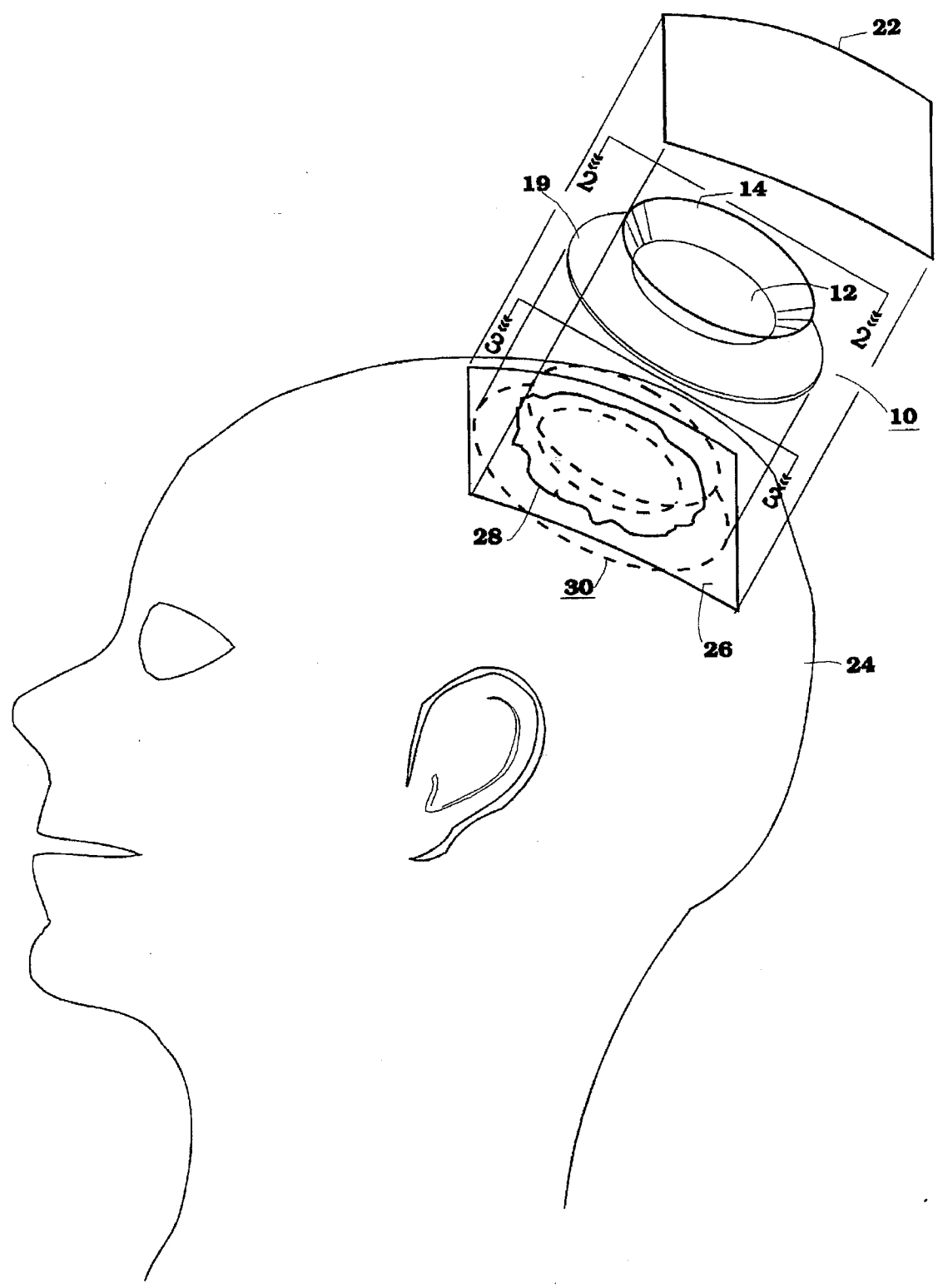
FIG. 1. is a perspective view of an embodiment of the invention showing the prosthesis in position for implantation in a patient.
Figure 2:
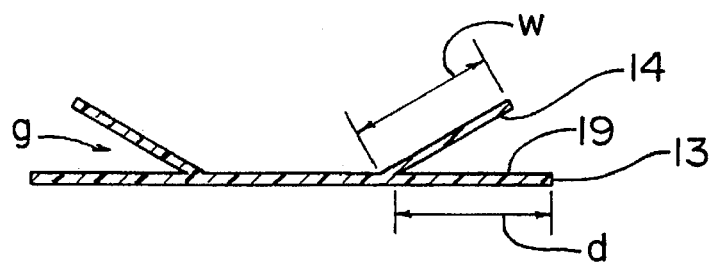
FIG. 2. is a cross section view of the embodiment shown in FIG. 1 taken along the line 2—2.
Figure 3:
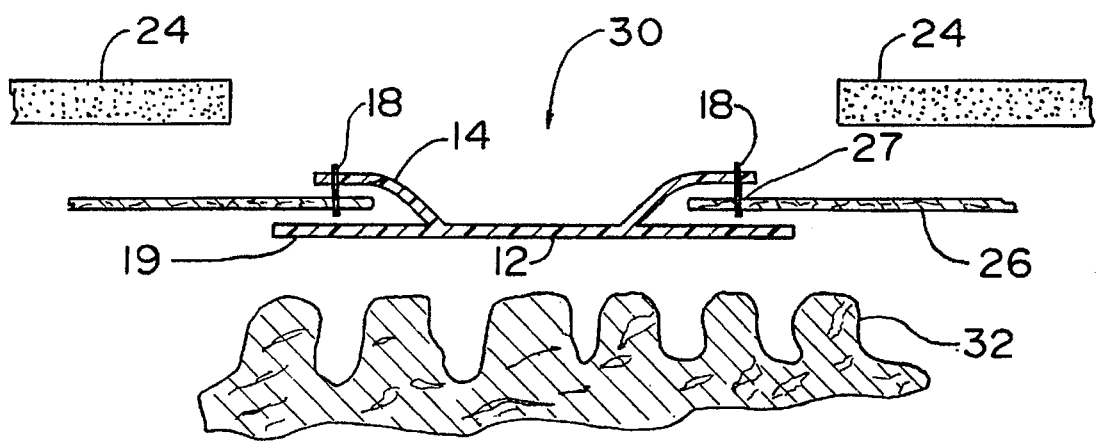
FIG. 3. is a cross section view taken along the line 3—3 in FIG. 1 showing the prosthesis implanted in a patient.

FIGS. 1-3 show one embodiment of the invention. The prosthesis 10 comprises a patch 12 of a material in sheet-like form, i.e., the cross section is generally thin and flat. The prosthesis further comprises a suture flange 14, preferably also in sheet-like form. The suture flange is attached to one side of the patch inward from the perimeter 13 of the patch by a distance, d, hereinafter the "lap distance" (FIG. 2). The patch includes a patch flange, which is the part of the patch extending inward from the perimeter by the lap distance. In cross section perpendicular to the plane of the patch, the suture flange and the patch flange 19 intersect at an angle facing the perimeter which defines a peripheral gap, g. The angle of intersection of the embodiment in FIGS. 1–3 is acute. That is, the angle is about 0°–89°. The suture flange and patch flange extend completely along the patch circumference.

FIG. 1 illustrates the method of using the prosthesis. Scalp, not shown, and bone flap 22 are removed from the surrounding skull 24 by conventional procedures to expose the dura 26. The dura may be deliberately cut to gain access to the underlying tissue or the dura may have been torn open by traumatic injury. In either case, following any appropriate operation on tissue beneath the opening, the dura is closed. In the case of multiple or ragged-edged openings often produced by injury, the dura is trimmed along a path 28 to define a single, generally smooth-edged opening. The implanted prosthesis, 30, is shown in phantom in FIG. 1 and in cross section in FIG. 3, with the patch beneath the dura and with the suture flange above the dura. The prosthesis size is selected such that the area of the patch is larger than the dural opening and that the width of the suture flange overlaps the lip 27 of the opening. The "lip" of the opening means the region of the dura immediately adjacent the edge of the opening. Generally, the lip extends up to about a centimeter away from the edge. In the embodiment shown in FIG. 3 the lip inserts in the peripheral gap. It is understood that, alternatively, the lip can lie over the suture flange as will be explained below. The physician then sews the lip of the dural opening to the suture flange with conventional sutures 18. Finally, the physician replaces the bone flap and scalp by methods known in the art.

Placement of the sutures is important. The sutures are disposed in a circuitous path along the lip of the opening to achieve an effectively leak-free closure of the dural sac. The sutures are located on the suture flange inboard of the patch perimeter 13. The patch flange is not perforated by the suturing instrument and the bottom floats of the sutures do not extend below the patch. "Bottom floats" means the segments of the suture threads which descend below the dura and suture flange. Thus, the patch flange shields the underlying neural structure 32 from the suturing perforations and from the suture thread. Consequently, scar from foraminous fibroblast growth is confined to the peripheral gap. The patch material is of a suitably lubricious and biologically benign material selected such that the fibroblast and scar do not adhere more than negligibly to the patch surface. Therefore, any scarring of the underlying neural structure is substantially unable to attach to the patch surface. The bottom floats are also blocked away from the underlying neural structure by the interposed patch flange. It is further understood that conventional suture threads are likely to support scar growth. If the bottom floats were exposed to the neural structure, as in conventional suture stitching previously mentioned, scar could form to anchor the neural structure to the suture threads. However, according to the present invention, scar tissue that adheres to suture threads is unable to reach the neural structure, and thus, cannot attach. Accordingly, this present invention advantageously enables the physician to use traditional suture thread.

Figure 4:
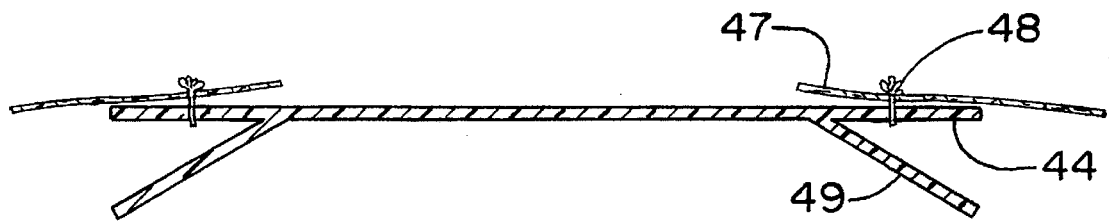
FIG. 4 is a cross section view of another embodiment of the invention in which the suture flange is in the same plane as the patch.

As indicated, the prosthesis can be constructed so that it is implanted wholly within the opening as shown in FIG. 4. In this embodiment, the dura 46 overlies both suture flange 44 and patch flange 49. Sutures 48 attach the lip 47 of the dura to the suture flange without penetrating the patch flange.

Figure 5:
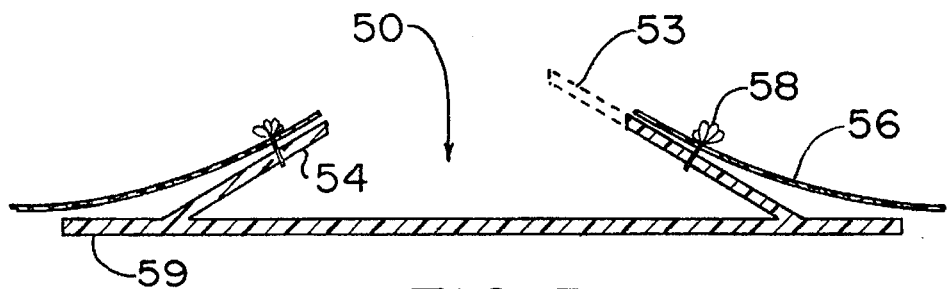
FIG. 5 is a cross section view of another embodiment of the invention in which the suture flange extends toward the center of the patch.

An another embodiment of the novel prosthesis 50 is shown in FIG. 5. It is seen that the angle of intersection between the suture flange 54 and the patch flange 59 is obtuse, i.e., about 91°–180°. Thus, the suture flange extends inwardly toward the center of the patch. The prostheses of FIGS. 4 and 5 are well suited to repairing an opening which is irregularly shaped or is much smaller than the cross section dimensions of the patch. In contrast, a portion or all of such a lip, would extend far into the peripheral gap of a prosthesis as in FIG. 3. Unless the dura is trimmed, the irregular or small opening would allow the lip to contact the junction of the suture flange and the patch flange in the gap. The contact would cause the lip to gather and fold upon itself. This would interfere with the ability to make a leak free seal. The whole prosthesis of FIG. 5, however, is placed inside the opening with the dura 56 lying above the suture flange and secured by sutures 58. Thus, it is unnecessary to trim the dura to fit within the peripheral gap. Any surplus 53 of the suture flange, which can be very wide, can be cut away and removed.

Figure 6:
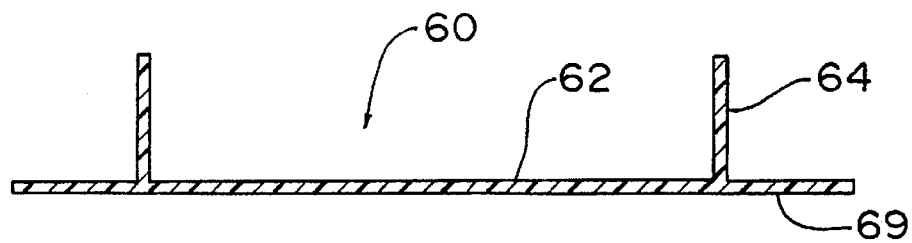
FIG. 6 is a cross section view of another embodiment of the invention in which the suture flange is attached in a perpendicular orientation.
Figure 7:
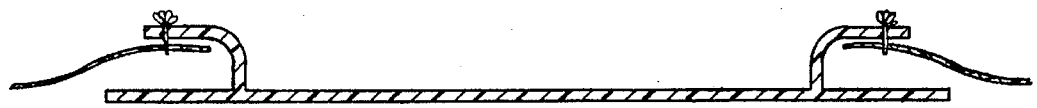
FIG. 7 is a cross section view of the embodiment of FIG. 6 shown with the suture flange flexed outwardly.
Figure 8:
FIG. 8 is a cross section view of the embodiment of FIG. 6 shown with the suture flange flexed inwardly.

FIG. 6 illustrates yet another embodiment of the novel prosthesis 60 wherein the suture flange 64 is attached in a perpendicular orientation, i.e., the angle of intersection between suture flange and patch flange 69 is about 90°. The material of this prosthesis, and especially, the suture flange is chosen to be highly flexible. Consequently, the suture flange can be flexed outwardly to form an acutely angled gap, as shown in FIG. 7, or inwardly to form an obtusely angled gap, as shown in FIG. 8. Thus, one size of this type of prosthesis can accommodate various opening sizes.

Figure 9:
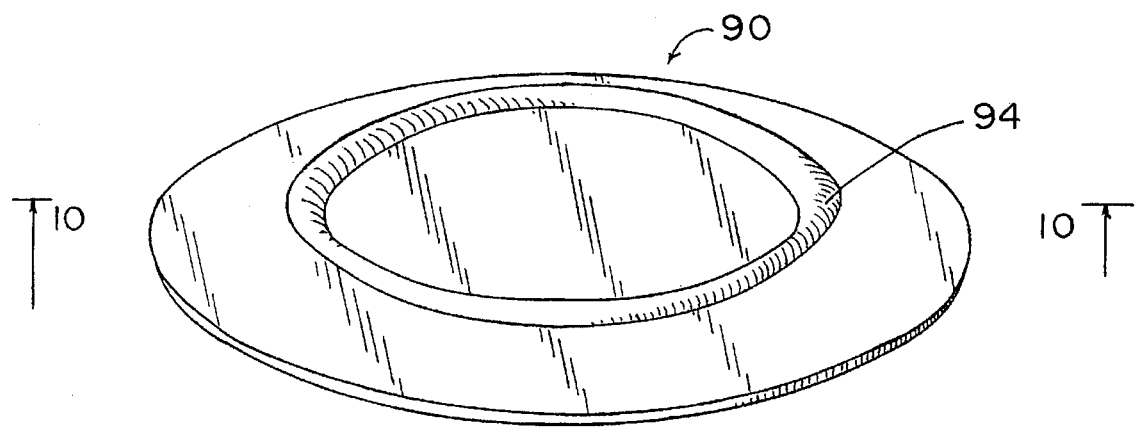
FIG. 9 is a perspective view of a ridged prosthesis according to this invention.
Figure 10:
FIG. 10 is a cross section view of the ridged prosthesis of FIG. 9 taken along line 10—10.
Figure 11:
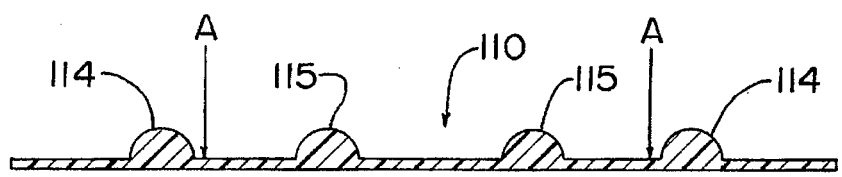
FIG. 11 is a cross section view of a multiple ridged prosthesis according to this invention.

Still another embodiment of the prosthesis 90 is shown in FIG. 9. The circular prosthesis is generally flat and includes a closed path, contiguous ridge 94 which corresponds to the suture flange. From FIG. 10, showing prosthesis 90 in cross section taken along line 10—10 of FIG. 9, it is seen that the ridge provides a bulge in the thickness of the prosthesis. The dura 106 is placed over the ridge and secured by sutures 108 which are sewn through the ridge and without descending below the patch. FIG. 11 illustrates in cross section a multiple ridge prosthesis 110 having an outer ridge 114 and an contiguous inner ridge 115. The multiple ridge prosthesis is adapted to fitting openings of different sizes. The prosthesis is inserted in the opening so that the lip overlies at least one ridge. The lip of a large opening will overlie only the outer ridge, while the lip of a small opening will overlie both ridges 114 and 115. For a small opening, prior to securing the prosthesis to inner ridge 115, the surgeon can cut completely through the prosthesis at the position shown by the arrows A to remove an annular piece that contains outer ridge 114. Although the figures illustrate ridged prosthesis having only one and two ridges, it is understood that prostheses having three or more ridges are contemplated according to the present invention. Similarly, prostheses having multiple suture flanges are also envisioned. The cross section shape of the ridge is not critical. A semicircular cross section is preferred. The diameter of the semicircular cross section will be about 1 to about 5 mm. The distance between adjacent ridges of a multiple ridge prosthesis is about 5 to about 30 mm, and preferably about 10 to about 20 min. The outermost ridge is distant from the perimeter by about 5 to about 30 mm, and preferably about 10 to about 20 mm. The ridges of the illustrated embodiments are circular and concentric to the perimeter of the circular patch. However, the ridges can be in any closed path, two dimensional configuration and can be eccentric to the patch perimeter. Likewise, the patch can be any geometric shape, as will be discussed, below.

Figure 12:
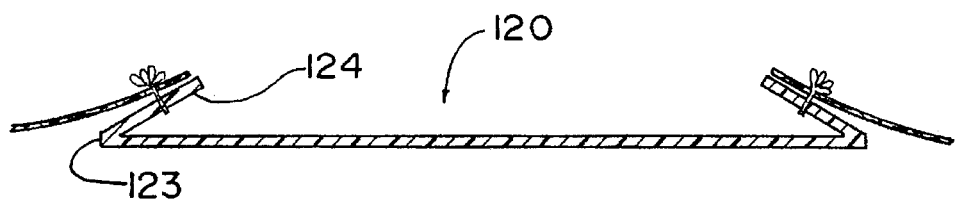
FIG. 12 is a cross section view of an embodiment of this invention having a suture flange attached at the perimeter of the patch.

A different embodiment of the novel prosthesis 120 is shown in FIG. 12. In this embodiment, the suture flange 124 is attached to the perimeter 123 of the patch and extends inwardly toward the center.

Figure 13:
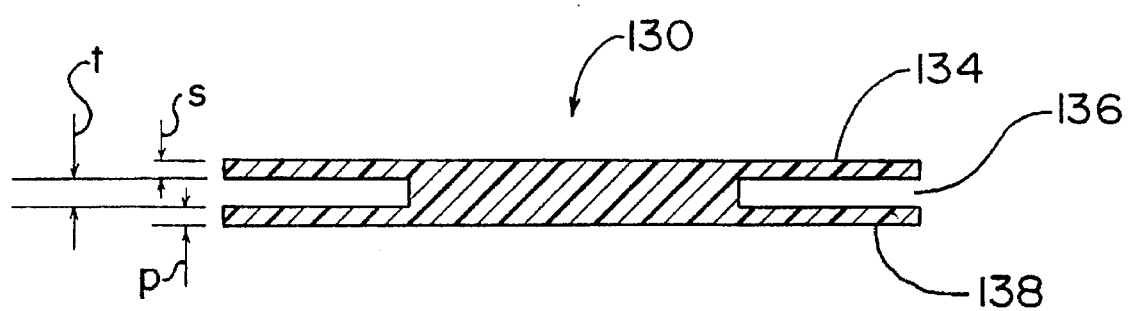
FIG. 13 is a cross section view of a prosthesis machined from a single sheet according to this invention.

FIG. 13 shows the cross section of yet another contemplated embodiment of the prosthesis according to this invention. The prosthesis 130 is a single sheet machined to form a circumferential slit 136 that defines the suture flange 134 and patch flange 138. The slit is substantially parallel to the plane of the sheet and has a substantially uniform thickness, t. The slit functions as the peripheral gap. FIG. 13 shows the slit located approximately equally distant from the surfaces of the prosthesis. The figure also shows the thicknesses of the suture flange and the patch flange being approximately equal to the thickness, t. Prostheses having different thickness dimensions are also contemplated.

Generally, the overall thickness of the embodiment according to FIG. 13 can be greater than that of the previously described embodiments because the overall thickness includes the slit thickness t as well as the thicknesses of the suture flange s and the patch flange p. Overall thickness of the prosthesis, i.e., s+t+p, is typically about 0.3 mm to about 10 mm and preferably, about 0.5 mm to about 5 mm. Each of the suture flange and patch flange thicknesses, s and p, is about 0.1 mm to about 1 mm, and preferably, about 0.3 mm to about 0.7 mm.

As indicated above, placement of the sutures in the suture flange is important to assure that the patch flange intervenes between underlying neural structure and the sutures. The width of the suture flange, w, FIG. 2 is less than the lap distance. This dimensional relationship assures that sutures are sewn through the suture flange inboard of the patch perimeter. A prosthesis having a suture flange greater than or equal to the lap distance is also contemplated; provided that the sutures are stitched through the suture flange inboard as previously described. Generally, each of the suture flange width and the lap distance is about 5 mm to about 30 mm, and preferably, about 10 mm to about 20 mm.

The previously described prostheses can be of autologous or heterologous animal tissue, such as dura from cadavers and porcine pericardium, or of effectively biologically benign, pliable synthetic material, such as polymer film and fabric. Although preferred for its high lubricity, animal tissue has certain disadvantages. For example, the supply of such tissue is limited; the tissue potentially exposes the donee to disease of the donor; and the donee may antigenically reject the patch. It is desirable to use lubricious (i.e., effectively nonadhesive to fibroblast growth), biologically benign synthetic materials, such as thermoplastic or thermosetting polymers, because they can be made in many shapes and sizes with consistent quality. Preferable, nonadhesive polymer materials suitable as the predominant component of polymeric prostheses according to this invention include highly halogenated, especially fluorinated, polyolefins, such as poly(tetrafluoroethylene) available under the tradename Teflon® and expanded poly (tetrafluoroethylene) available under the tradename Goretex™. It is understood that the polymer material can include blends of different polymers and polymer compounds containing additives and fillers, such as plasticizers, known in the art to facilitate the manufacture of polymer articles and for modifying the properties of polymers.

Thermoplastic polymer can be molded, and, in the case of thermoset polymer also cured, to provide a one piece prosthesis such that the suture flange is integral to the patch. Also, the suture flange can be bonded to the patch with adhesive or via thermal fusion. A fabric patch is also contemplated, with the proviso that the fabric be woven in a sufficiently tight weave that cerebrospinal fluid and fibroblast growth do not penetrate the interstices between yarns.

Figure 14:
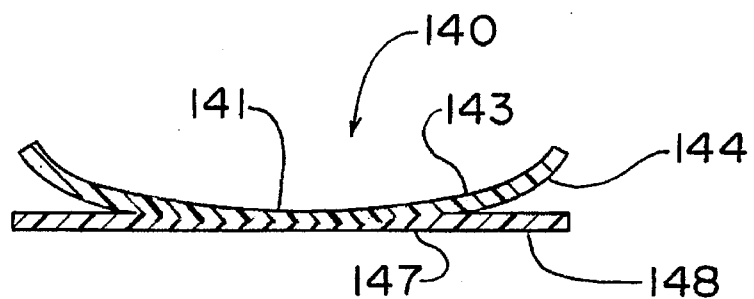
FIG. 14 is a cross section view of a multilayer composite prosthesis according to this invention.

Another embodiment of the prosthesis according to the present invention is shown in FIG. 14. This prosthesis 140 is a multilayer composite comprising a suture flange sheet 143 and a patch sheet 147 which are laminated in a central region 141 and separated near the perimeter. The separation between sheets provides the peripheral gap and defines the suture flange 144 and the patch flange 148. The sheets are laminated by adhesive or by fusion, for example. Laminated construction readily enables production of diverse size and shape patches. Preferably, the materials of the laminated prosthesis are synthetic polymers.

The suture flange and patch sheets can be of different materials. The materials can be selected to optimally perform the respective desired functions of each sheet. For example, the suture flange sheet material can be chosen for strength and ease of stitching. Preferably, the suture flange material should also adhere well to the dura and promote fibroblast ingrowth. These characteristics promote the formation by the body of a very strong attachment during healing to hold the patch firmly in place. Preferred suture flange sheet materials include, for example, film or fabric of thermoplastic polyester, such as polyethylene terephthalate and of thermoplastic copolyetherester elastomers available from DuPont under the tradename Hytrel®. Strong attachment can also be accomplished by choosing a suture flange sheet of a bioresorbable material. Bioresorbable materials, such as poly(glycolic acids) gradually and benignly decompose within the body over a sufficient time to allow fibroblast tissue to grow over and fix the patch in place. The patch sheet material of such a multilayer composite prosthesis of course would be nonresorbable and would be selected for a good ability to resist adhesion by scar tissue.

As mentioned the prosthesis of this invention is useful for patching an opening in the dura mater. Additionally, the novel prosthesis will find utility for closing holes in diverse types of connective tissue membranes throughout human and animal bodies. For example, the prosthesis can be used for correcting hernial defects and for patching the pericardium.

The prosthesis of this invention can be formed in many geometric shapes and sizes to fit various openings. Circular and triangular shapes are preferred for holes having approximately equal length and width, such as are typically encountered in heart surgery and craniotomy. An elliptical patch is preferred for hernial and spinal dura repair which generally involves an elongated opening.

Generally, the novel prosthesis is pliable for conformation to rough and irregular, as well as substantially planar, membrane surfaces. Slightly stiff and shaped prostheses are also contemplated for special applications. For example, an elongated, slightly curved, concave surface prosthesis, shaped like a portion of the surface of a cylinder is believed useful for spinal dura openings.

I claim:

1. An implantable prosthesis comprising
   a patch of lubricious, biocompatible material having a perimeter a portion of said patch defining a flange which extends inward from the perimeter by a lap distance; and
   a suture flange attached to one side of said patch, wherein said suture flange overlaps said patch flange to minimize scar tissue adhesion between body connective tissue membranes and adjacent organ tissue, wherein the patch flange and the suture flange extend along the whole perimeter.

2. The prosthesis of claim 1 wherein the lap distance is in the range from about 5 mm to about 30 min.

3. The prosthesis of claim 2 wherein the suture flange is at most as wide as the patch flange.

4. The prosthesis of claim 3 wherein the patch is predominantly a material selected from the group consisting of polymer film and body fluid impenetrable fabric.

5. The prosthesis of claim 4 wherein the polymer is a highly fluorinated olefin polymer.

6. The prosthesis of claim 5 wherein the polymer is expanded poly(tetrafluoroethylene).

7. The prosthesis of claim 3 wherein the suture flange is attached to the patch inward from the perimeter by the lap distance, wherein the patch has a flat surface defined by a plane, and wherein the suture flange and the patch flange intersect in a direction perpendicular to the plane at an angle which defines a gap.

8. The prosthesis of claim 7 wherein the angle is acute.

9. The prosthesis of claim 7 wherein the angle is obtuse.

10. The prosthesis of claim 7 wherein the angle is about 90 degrees and wherein the the suture flange is flexed to form a gap of an angle in the range of about 0–180 degrees.

11. The prosthesis of claim 1 wherein the prosthesis is a multilayer composite including;

a patch sheet; and a suture flange sheet laminated to the patch sheet in a central region and separated from the patch sheet near the perimeter.

12. The prosthesis of claim 11 wherein the suturing sheet is of a material different from the patch sheet.

13. The prosthesis of claim 1 wherein the prosthesis comprises a single flat sheet having a surface defined by a plane, said sheet being machined to form a circumferential slit that defines the suture flange and the patch flange.

14. The prosthesis of claim 13 wherein the suture flange and the patch flange are substantially parallel to the plane and wherein the circumferential slit has a substantially uniform thickness.

15. The prosthesis of claim 14 wherein the prosthesis has an overall cross section thickness in the range from about 0.3 mm to about 10 mm.

16. The prosthesis of claim 1 wherein the patch is circular.

17. The prosthesis of claim 1 wherein the patch is elongated.

* * * * *